United States Patent [19]
Eckstrom

[11] Patent Number: 5,747,809
[45] Date of Patent: May 5, 1998

[54] NDIR APPARATUS AND METHOD FOR MEASURING ISOTOPIC RATIOS IN GASEOUS SAMPLES

[75] Inventor: Donald J. Eckstrom, Portola Valley, Calif.

[73] Assignee: SRI International, Menlo Park, Calif.

[21] Appl. No.: 661,482

[22] Filed: Jun. 11, 1996

[51] Int. Cl.[6] .................... G01N 21/31; G01N 21/35; G01N 21/61
[52] U.S. Cl. .................. 250/345; 250/343; 250/339.13
[58] Field of Search ...................... 250/345, 343, 250/339.13; 128/719

[56] References Cited

U.S. PATENT DOCUMENTS

| | | |
|---|---|---|
| 3,950,101 | 4/1976 | Dewey, Jr. ................. 250/345 |
| 4,298,347 | 11/1981 | Walsh ........................ 23/230 |
| 4,829,183 | 5/1989 | McClatchie et al. ............ 250/345 |
| 5,102,806 | 4/1992 | Mikasa et al. ................ 250/343 |
| 5,317,156 | 5/1994 | Cooper et al. ................ 250/345 |
| 5,394,236 | 2/1995 | Murnick ...................... 356/111 |
| 5,479,019 | 12/1995 | Gross ........................ 250/345 |
| 5,486,699 | 1/1996 | Fabinski et al. .............. 250/345 |
| 5,572,032 | 11/1996 | Fujiwara et al. .............. 250/343 |
| 5,585,636 | 12/1996 | Dollansky .................... 250/343 |

*Primary Examiner*—Michael J. Tokar
*Assistant Examiner*—Virgil O. Tyler
*Attorney, Agent, or Firm*—LeeAnn Gorthey

[57] ABSTRACT

An apparatus for measuring isotopic ratios provides four separate optical paths for separate measurement of each of two isotopes relative to a reference signal, using spectrally resolved infrared radiation. The design permits the measurements to be made accurately without significant time lags between measurements, and without interchanging of cells or filters.

23 Claims, 5 Drawing Sheets

NDIR APPARATUS AND METHOD FOR MEASURING ISOTOPIC RATIOS IN GASEOUS SAMPLES

FIELD OF THE INVENTION

The present invention relates to an apparatus and method for measuring isotopic ratios in gaseous samples by non-dispersive infrared (NDIR) spectroscopy.

REFERENCES

Cooper, D. E., pu Applied Optics 32:6727–6731 (1993).

Cooper, D. E. et al., U.S. Pat. No. 5,317,156 (1994).

Fabinski, W. et al., U.S. Pat. No. 5,486,699 (1996).

Graham, D. Y. et al., *Lancet* 1987:1174–1177 (5/1987).

Ghoos, Y. F. et al., *Gastroenterology* 104:1640–1647 (1993).

Gross, J., U.S. Pat. No. 5,479,019 (1995).

M. Haisch et al., *Isotop. Environ. Health Stud.* 30:253–257 (1994).

Kato, H. et al., *Am. J. Gastro.* 88:64–69 (1993).

King et al., *Gastroenterology* 91:1447–1451 (1986).

Lacroix, M. et al., *Science* 181:445 (1973).

Lambert, G. H. et al., *Environmental Health Perspectives* 89:175–181 (1990).

Lee, P. S. et al., U.S. Pat. No. RE 33,493 (1990).

Link, W. T., U.S. Pat. No. 3,725,701 (1973).

Macken, J. A., U.S. Pat. No. 4,756,000 (1988).

Macken, J. A., U.S. Pat. No. 4,757,512 (1988).

Marshall, B. et al., U.S. Pat. No. 4,830,010 (1989).

Mion, F. et al., *Life Sciences* 54:2093–2098 (1994).

Murnick, D. E. et al., *Science* 263:945–947 (1994).

Murnick, D. E. et al., U.S. Pat. No. 5,294,236 (1995).

Schoeller, D. A. et al., *J. Appl. Physiology* 53:955–959 (1982).

Shreeve et al., *Gastroenterology* 71:98–101 (1976).

Shulman et al., *Pediatric Res.* 16:177A (1982).

Waterlow et al., *Amer. J. of Physiology* 235:E165–E174 (1978).

Watkins, J. S. et al., *J. Lab. Clin. Med.* 90:422–430 (1977).

Watkins, P. E. et al., *Clin. Pharmacol. Ther.* 48:120–129 (1990).

Witteman, W. J., *Appl. Phys. Lett.* 11:337 (1967).

BACKGROUND OF THE INVENTION

Methods for precise measurement of isotopic ratios have long been of value in the fields of geology and archaeology, e.g., in carbon dating. Isotopically labelled substances are also used in the study of metabolic processes and chemical mechanisms. Stable isotopes, such as $^{13}C$ and $^{15}N$, are particularly useful in medical applications. For example, the presence of the bacterium *H. pylori*, which has been shown to cause stomach ulcers, can be detected by measuring the $^{13}CO_2/^{12}CO_2$ ratio in the breath of a patient following ingestion of $^{13}C$-labeled urea (Marshall, Graham). A number of other disorders can be diagnosed by breath analysis following ingestion of the appropriate $^{13}C$-labeled substance, as discussed further below. These include fat malabsorption, liver disfunction, ileal disfunction, and small intestine bacterial overgrowth.

Mass spectrometry has been widely used in the past for isotopic ratio analysis because of its high selectivity and sensitivity, which is important in many medical applications. However, the instrumentation is expensive, and sample preparation and analysis can be complex. Laser techniques (e.g. Murnick, Cooper, Lee) have also been described for measurement of the $^{13}CO_2/^{12}CO_2$ ratio. Such methods, however, also use complex and expensive equipment, and suitable lasers are not always available for all desired wavelengths.

Trace amounts of infrared active gases, such as $CO_2$, CO, $NO_x$, or $CH_4$, can be routinely detected by non-dispersive infrared (NDIR) spectroscopy. Conventional NDIR typically employs a blackbody infrared radiation source and a filter wheel containing filters restricting the radiation to a range of wavelengths particular to the species being measured. The filtered IR radiation passes through a gas sample, where it is absorbed in proportion to the amount of that species present, and falls on a detector, which measures the fraction of radiation transmitted. Alternatively, the radiation may be filtered after passing through the gas sample. An unattenuated reference signal may also be generated by including a filter which restricts radiation to a range where no absorption occurs.

While absorption ranges of different gases are generally easily resolved, the spectral bands of isotopic species of the same gas frequently overlap. Thus, conventional NDIR is not effective for measurement of isotopic ratios, especially when one isotope is present at a significantly greater concentration. NDIR spectrometry is also subject to errors resulting from the time lag between sample and reference measurements, temperature fluctuations within the apparatus, which can arise from multiple moving parts or power sources, and/or drift in the intensity of the source temperature. Such errors may be acceptable in measuring separate molecular species, but not in distinguishing isotopes, particularly at the precision required for many medical diagnostic applications.

Temperature control is of particular importance in cases where the overlap of absorption bands of isotopic species, noted above, may not be totally avoidable even with carefully resolved source radiation. Corrections made to eliminate this "crosstalk" can be strongly dependent on the sample temperature. For example, in $^{13}CO_2/^{12}CO_2$ measurements, calculations suggest that the sample temperature must be held to within 1° C. or less, and preferably closer to within 0.1° C., in order that the crosstalk correction be smaller than the precision necessary to make measurements for certain medical diagnostic purposes.

Several approaches have been taken to increasing the precision of NDIR measurement of isotopic ratios in gases, particularly the $^{13}CO_2/^{12}CO_2$ ratio in $CO_2$. These include, for example, Fabinski et al., which describes the use of a two beam instrument for measuring the $^{13}CO_2/^{12}CO_2$ ratio in a gaseous sample. An optical filter filled with $^{12}CO_2$ is placed in the optical path measuring $^{13}CO_2$ to remove radiation in the $^{12}CO_2$ absorption band which overlaps and interferes with measurement of absorption in the $^3CO_2$ absorption band. Vessels filled with the respective isotopes may be swung in and out of the optical paths for calibration purposes. Two separate optoacoustic detectors, one for each isotope, are used.

This method requires a separate detector for each species being measured. The calibration method incorporates a significant time lag between calibration of the detectors and actual measurement of the sample, and also adds moving parts to the apparatus, which can cause temperature fluctuations. Crosstalk corrections are required in the method described by Fabinski. As noted above, such corrections can be strongly dependent on the sample temperature.

Gross also describes a two-beam instrument which employs filter cells filled with a single isotope, i.e., $^{13}CO_2$ or $^{12}CO_2$, respectively, to remove corresponding spectral frequencies from broad band IR radiation transmitted through the filter cells. The radiation subsequently passes through a sample cell, which also serves as an optopneumatic detector cell. Because reference cells, when provided, lie in the same optical paths as the sample and filter cells, reference measurements must be made separately from sample measurements, thus incorporating a significant time lag. The sample size is also limited by the capacity of the detectors, which could cause problems in obtaining a uniform sample in breath analysis, and in measuring low concentration species such as $^{13}CO_2$.

None of the above methods, therefore, adequately addresses the problems of error and lack of reproducibility caused by time lag between measurements and the resulting signal drift, or by temperature fluctuation, in NDIR measurement of isotopic ratios, where high precision is needed.

SUMMARY OF THE INVENTION

The present invention includes, in one aspect, an apparatus for measuring the ratio of first and second isotopic species of an analyte molecule in a gaseous sample by non-dispersive IR spectroscopy. The apparatus contains one or more sources of IR radiation, at least one sample cell containing the gaseous sample, at least one reference cell free of the analyte molecule, and one or more IR detectors. The apparatus also provides four optical paths of IR radiation impinging on the detector or detectors. The four optical paths specifically include: a first sample path traversing a sample cell and having a first wavelength range characteristic of the first isotopic species, a first reference path traversing a reference cell and having a first wavelength range characteristic of the first isotopic species, a second sample path traversing a sample cell and having a second wavelength range characteristic of the second isotopic species, and a second reference path traversing a reference cell and having a second wavelength range characteristic of the second isotopic species. The apparatus also contains a mechanism for directing radiation through each of the cells and onto the detector or detectors, and shutters or other similar structures to permit radiation to traverse each of the optical paths in rapid succession. The apparatus of the invention allows the ratio of isotopic species in the gaseous sample to be determined by comparison of the intensity of radiation impinging on the detector or detectors from the four optical paths.

In preferred embodiments, the apparatus contains one or more of the following: a single source of IR radiation, a single detector, IR transparent lenses for directing radiation through the optical paths and onto the detector, and vacuum activated shutters.

In one embodiment, the four optical paths are provided by the use of bandpass filters. Specifically, filters are positioned in the first sample path and the first reference path which restrict the IR radiation transmitted to the detector or detectors from these paths to a narrow wavelength range characteristic of the first isotopic species. Similarly, filters are positioned in the second sample path and the second reference path which restrict the IR radiation transmitted to the detector or detectors from these paths to a narrow wavelength range characteristic of the second isotopic species.

In another embodiment, the apparatus contains two spectrally resolved sources of IR radiation. The first spectrally resolved source contains the first isotopic species of the analyte molecule, which is vibrationally excited, thereby causing it to radiate at one or more wavelengths characteristic of the first species. Similarly, the second spectrally resolved source contains the second isotopic species of the analyte molecule, which is vibrationally excited, thereby causing it to radiate at one or more wavelengths characteristic of the second species. The molecules of the isotopic species may be vibrationally excited via an electronic discharge, in which case the electronic discharge may be electronically modulated, or via an external heat source.

In a preferred embodiment, the apparatus contains a first pair of cells, that is, a first sample cell and a first reference cell, and a second pair of cells, that is, a second sample cell and a second reference cell. This embodiment preferably includes a flow path entering one of said sample cells, connecting the sample cells, and exiting the other sample cell, such that the gaseous sample is maintained at a composition and pressure which is equal in the two sample cells. In the case where the first isotopic species of the analyte molecule has a greater natural abundance than the second isotopic species, the first sample cell is preferably correspondingly shorter in length than the second sample cell.

In a preferred embodiment, the sample and reference cells are contained within an enclosure effective to control cell temperature to within approximately 0.1° C. Preferably, a mechanism is provided to remove any ambient analyte molecule from this enclosure.

In one embodiment of the invention, the analyte molecule is $CO_2$, the first isotopic species is $^{12}CO_2$, and the second isotopic species is $^{13}CO_2$.

In another aspect, the invention provides a method for measuring the ratio of first and second isotopic species of an analyte molecule in a gaseous sample by non-dispersive IR spectroscopy. In accordance with the method, IR radiation is transmitted through four optical paths which impinge on an IR detector or detectors. The optical paths include, specifically, a first sample path traversing a sample cell and having a first wavelength range characteristic of the first isotopic species, a first reference path traversing a reference cell and having a first wavelength range characteristic of the first isotopic species, a second sample path traversing a sample cell and having a second wavelength range characteristic of the second isotopic species, and a second reference path traversing a reference cell and having a second wavelength range characteristic of the second isotopic species. The method further includes determining the concentration of the first isotopic species from the intensity of radiation received at the detector from the first sample path relative to the intensity of radiation received at the detector from the first reference path, and, similarly, determining the concentration of the second isotopic species from the intensity of radiation received at the detector from the second sample path relative to the intensity of radiation received at the detector from the second reference path. The ratio of the isotopic species in the gaseous sample is then determined from these respective concentrations.

In a preferred method, each of the optical paths is traversed by radiation in repeated rapid succession. In one embodiment of the method, the four optical paths are provided by the use of bandpass filters. Specifically, filters are positioned in the first sample path and the first reference path which are effective to restrict the IR radiation transmitted to the detector or detectors from these paths to a narrow wavelength range characteristic of the first isotopic species. Similarly, filters are positioned in the second sample path and the second reference path which are effective to restrict the IR radiation transmitted to the detector or detectors from these paths to a narrow wavelength range characteristic of the second isotopic species.

In an alternate embodiment, the four optical paths are provided by vibrationally exciting each isotopic species, causing each species to emit radiation at one or more characteristic wavelengths, and directing each of the resulting beams of radiation through a sample cell and a reference cell, respectively.

A preferred method further includes the step of correcting for crosstalk, which may result from absorption of one isotopic species at a wavelength range characteristic of the other isotopic species.

In one embodiment of the method, the analyte molecule is $CO_2$, the first isotopic species is $^{12}CO_2$, and the second isotopic species is $^{13}CO_2$.

In one aspect, the method may be used for breath analysis. In this case, the gaseous sample is made up of the expired breath of a subject to whom an isotopically labelled substance has been previously administered. The ratio of isotopes in the expired breath sample may provide information as to, for example, the metabolism of the labelled substance by the subject.

These and other objects and features of the invention will become more fully apparent when the following detailed description of the invention is read in conjunction with the accompanying drawings.

DETAILED DESCRIPTION OF THE INVENTION

I. Definitions

Terms below have the following meanings unless otherwise indicated:

A "spectrally resolved source" is a radiation source that produces radiation limited entirely or primarily to one of the absorbing species being analyzed, generally by incorporation of the absorbing species into the source.

"Spectrally resolved radiation" is radiation that is limited in whole or in part to the absorbing frequencies of one of the absorbing species being analyzed. It may be produced by a spectrally resolved source, as defined above, or by resolution, e.g. by bandpass filters, of broad band radiation from a conventional radiation source. "Analyte molecule" refers to the molecule whose isotopic ratio is being determined, and thus includes all isotopes, also referred to as "isotopic species", of the molecule.

An "optical path" is a path of radiation originating at a source, passing through a sample cell or a reference cell, and arriving at a detector. An optical path is either a "sample path", which passes through a sample cell, or a "reference path", which passes through a reference cell.

Radiation "characteristic of" a given isotopic species refers to radiation covering a range of wavelengths at which the given species absorbs, and at which absorption of the other isotopic species being measured is preferably minimal.

II. NDIR Apparatus

A. General Layout

Figure 1:
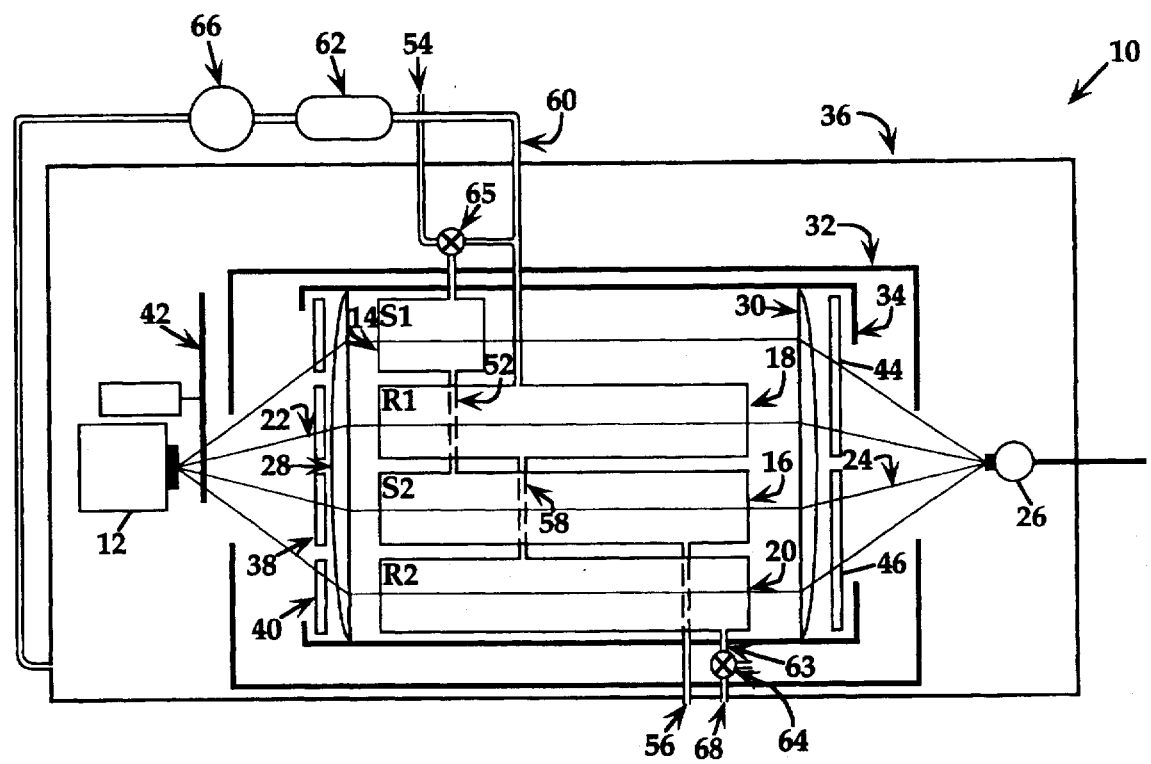
FIG. 1 shows a schematic of an NDIR apparatus constructed according to one embodiment of the invention.

FIG. 1 illustrates an NDIR apparatus 10 constructed in accordance with one embodiment of the invention. In this embodiment, the apparatus contains a source 12 of broad band IR radiation, which may be, for example, a tungsten filament. The current passing through the filament in the radiation source may be regulated to stabilize the intensity of the source.

Radiation from the source is able to traverse one or more sample cells and one or more reference cells. The reference cells are free of the analyte molecule, and may contain purified air or other gas from which the analyte molecule has been removed, or they may be evacuated. A preferred embodiment contains one sample cell for each species being measured, as shown at 14 and 16, and one reference cell for each species, as shown at 18 and 20. Thus, four separate optical paths, such as paths 22,24, are provided for measurement of the ratio of two isotopic species.

Figure 2:
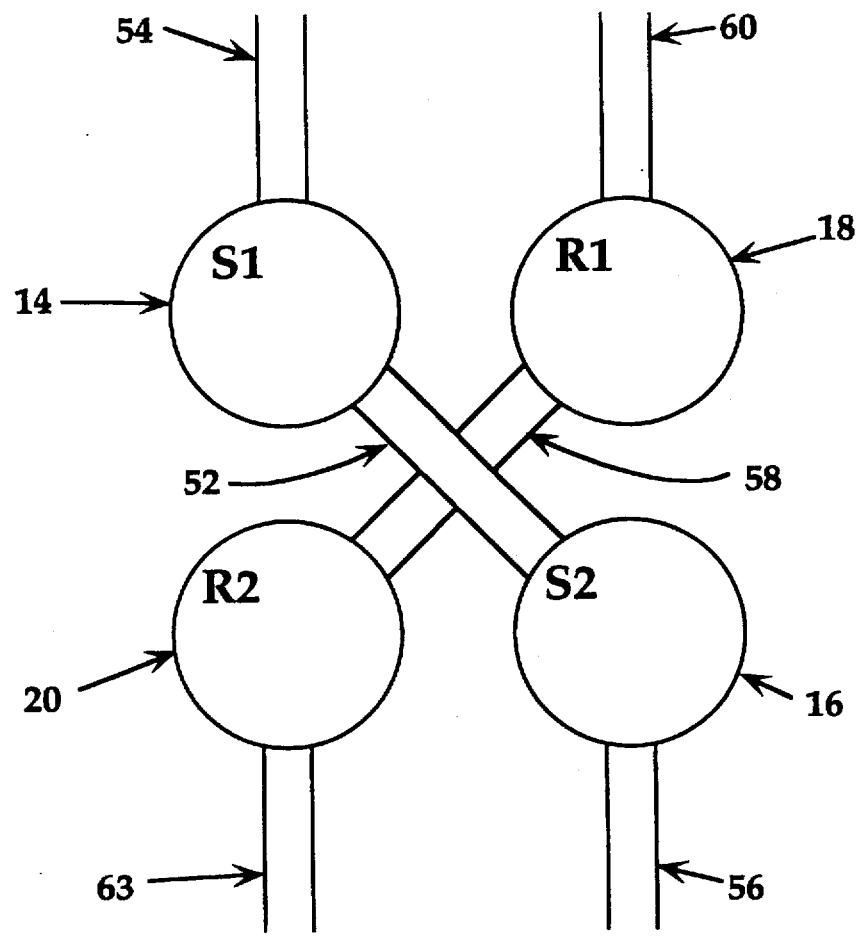
FIG. 2 shows an end view of cells arranged in two tiers within the apparatus.
Figure 3:
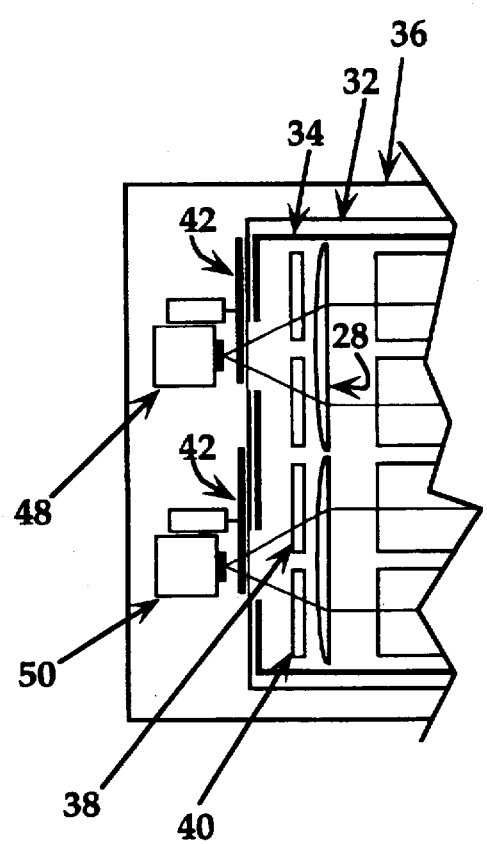
FIG. 3 shows two spectrally resolved sources, in accordance with one embodiment of the invention.

FIGS. 1 and 3 show the cells arranged in one plane for clarity; however, in practice, the cells will typically be arranged, for example, as shown in FIG. 2, as discussed further below.

Although four separate cells are shown, and are preferred in practice, it will be appreciated from the following description that different cell configurations could be employed as long as they allow measurement of radiation traversing the four separate optical paths described above. For example, one physical cell could be designed to accommodate two optical paths.

When the isotopic species of the analyte molecule differ greatly in abundance, it is advantageous to have two sample cells of correspondingly different lengths. The greater abundance isotope is measured in a shorter cell, as shown at 14, to avoid saturation of the absorbance measurement. The ratio of cell lengths is preferably such that the resulting absorbances of radiation occurring in each cell are of comparable magnitude. If spectral filters are used to resolve the transmitted radiation, as described below, the absorbance of the greater abundance isotope may also be reduced by selecting a low-intensity portion (e.g. an edge) of the absorption band.

One or more detectors, such as detector 26, detects radiation transmitted through the cells from the source. The detector is preferably a solid state photoconductive or photovoltaic IR detector. An optopneumatic detector could also be used. A single detector is preferred, in order to give maximum consistency in signal detection and processing.

Methods of directing beams of radiation typically include, for example, systems of mirrors or other light guides. A separate source could also be used for each path, although such a design increases the possibility of variation in the intensity of source radiation, so that a minimum number of sources is generally preferred. In a preferred embodiment, collimating and focusing IR-transparent lenses, such as shown at 28 and 30, serve to direct radiation from the source or sources, through the cells and onto the detector. As noted above, the cells are shown in one plane in FIGS. 1 and 3 for clarity. However, in practice, for the purpose of collimating and focusing, the cells are arranged such that each optical path intercepts the lens at a point equidistant from the lens centerline. This can be accomplished by two tiers of cells, as shown, for example, in the end view shown in FIG. 2. The lenses may also serve as entrance and exit windows, respectively, for the sample and reference cells.

To maximize temperature control, the cells and adjacent components are preferably contained in a temperature-regulated environment. In the embodiment shown in FIG. 1, this is provided by a double thermal oven, consisting of an outer heater 32 and an inner heater 34. Preferably, the double thermal oven is effective to control cell temperature to within 0.1° C. The heaters are provided with openings through which the source radiation passes. Studies in support of the invention show that sufficient temperature control can be maintained within such an oven when samples or purge gas (described below) are introduced at ambient temperatures.

A further enclosure 36 holds the double thermal oven, source(s), chopper(s), and detector(s), as shown in FIG. 1. This enclosure may be continually or intermittently purged with purified air or other purge gas, or it may be evacuated. Other structural features may also be included to maximize temperature stability, such as a floor and supports made of insulating material, e.g. ceramic or plastic, and a heat sink adjacent to the detector.

In operation of the apparatus, the four optical paths are exposed to radiation in a rapid repeated sequence, as discussed further below. In a preferred embodiment, this exposure is controlled via vacuum-activated shutters, as shown, for example, at 38, 40. A small pump (not shown) outside the enclosure 32 draws vacuum on a manifold containing four microvalves, which control the shutters. Such a design allows the shutters to be operated by external control and with minimal temperature fluctuations. The shutters may also be controlled by electromechanical solenoids, although these can cause temperature excursion by dissipation of power in the vicinity of the cells.

A chopper 42 is provided to modulate the source radiation. The chopper is the only major moving part within the apparatus, and in certain embodiments may be replaced by electronic modulation, as described below.

B. Radiation Sources

In accordance with the present invention, the absorbance of radiation characteristic of different isotopic species in a gaseous sample is accurately determined by measuring the intensity of radiation characteristic of each species transmitted through a sample cell and a reference cell, respectively. For this purpose, four separate optical paths are provided. The optical paths include, specifically, a first sample path and a first reference path, through which radiation characteristic of the first isotopic species is transmitted, and a second sample path and a second reference path, through which radiation characteristic of the second isotopic species is transmitted.

Such a design allows isotopic species of a sample molecule to be measured as separate species, without the necessity of interchanging cells or filters, and without incurring significant delays between the respective absorbance measurements. As discussed above, this eliminates significant sources of signal drift or temperature fluctuations (due to moving parts within the apparatus), which can introduce errors into the measurement of isotopic ratios.

1. Single Source with Bandpass Filters. With reference to FIG. 1, radiation from a single source may be resolved by passing it through a filter, such as filters shown at 44 and 46, which restricts the radiation reaching the detector to a narrow wavelength range characteristic of one or the other isotopic species.

According to one embodiment of the invention, the radiation entering each cell may be first spectrally resolved (filtered) so that it is exclusively or at least predominantly absorbed by only one or the other of the isotopic species being measured.

Alternatively, broadband radiation may be passed through the cells, with the radiation then limited to a wavelength range characteristic of one or the other of the isotopic species before it reaches the detector. In this embodiment, the filters are located between the cells and the detector, as shown in FIG. 1. In either case, the radiation impinging on the detector from each sample cell is spectrally resolved such that it has been absorbed exclusively or at least predominantly by only one or the other of the isotopic species being measured.

Wavelength ranges are chosen for the separate isotopes that are non-overlapping to the greatest extent possible, while being absorbed strongly enough by each species to give a consistent and reliable measurement. In cases where some overlap nonetheless occurs, especially when a greater abundance isotope interferes with the absorbance measurement of a lesser abundance isotope, correction may be made for such "crosstalk" effects, as described below in Section III.

2. Isotope-Specific Spectrally Resolved Sources. Spectrally resolved radiation may also be produced by incorporating the isotopic species itself into the source. In this embodiment, multiple sources, preferably one per isotopic species, are provided, such as sources 48, 50 in FIG. 3. (Other elements of the apparatus, not shown in FIG. 3, are similar to those shown in FIG. 1). The isotopically pure gas is preferably contained within a cell made of IR-transparent material, or with windows made of such material. Radiation at the characteristic IR wavelengths of a given isotopic species is produced by vibrationally exciting the molecules of the pure isotope, thus causing them to radiate at these specific wavelengths.

One efficient means of producing highly vibrationally excited molecules is via an electronic discharge. The discharge may be created by various means such as a direct current, alternating current, radio frequency, or microwave excitation. One advantage of this radiation source is that the radiation may be modulated electronically, rather than mechanically by means of a chopper. This modification eliminates the major moving part within the apparatus.

The isotopically pure gas is preferably admixed, at a low concentration, with one or more inert gases such as helium and/or nitrogen. The concentration is preferably less than 10%, and more preferably less than 1%. A low concentration increases the efficiency of the light source by minimizing the re-absorption of radiation by molecules of the gas. Positioning the source of the discharge, e.g. an electrode, close to an exit window through which the radiation is emitted, also reduces such re-adsorption.

Although decomposition of the source gas can occur in such a discharge, this problem can be addressed through selection of the gas composition and materials of construction of the source, as described, for example, in Witteman. In Witteman, platinum electrodes are employed in a $CO_2$ laser to increase the lifetime of the source. Other catalysts such as gold and silver oxide (Macken) have also been used in $CO_2$ lasers, to catalyze the reformation of $CO_2$ from CO and $O_2$.

The isotopically pure gas may also be vibrationally excited by thermally heating, e.g. by an external oven, to a temperature of 500° C. or more, or preferably 1,000° C. or more. In this case, admixture with inert gases is not required. Heated surfaces are configured such that they do not cross the optical paths of radiation emitted from the source to the sample and reference cells.

By using separate sources incorporating the isotope of interest, as described, radiation is produced only at the specific wavelengths characteristic of this isotope, and thus will be absorbed only by this isotope in the sample path. This differs from the use of filters, described above, which limits the radiation to a narrow, but still continuous, range. Thus the problem of crosstalk is generally addressed more effectively by the use of separate spectrally resolved sources.

In some cases it may be desirable to combine the use of spectrally resolved sources and bandpass filters. One advantage of the use of filters is the possibility of centering the desired range of wavelengths at a location other than the center of the absorbance band. Thus, if crosstalk is still a problem at certain wavelengths, even with resolved source radiation, these wavelengths may be avoided by the use of filters. Also, as noted above, a very strong absorbance signal (as for a high abundance isotope) may be attenuated by measuring the edge of an absorption band.

C. Configuration of Flow Paths

In a preferred configuration, as shown in FIG. 1, a first sample cell is connected to a second sample cell via a conduit 52, and to an outside inlet 54 (also shown in FIG. 2). The outside inlet may be opened to the atmosphere such that the sample is introduced at atmospheric pressure, filling first one sample cell and then the other. This ensures a uniform composition and pressure of the gaseous sample between the cells. For use in breath analysis, the sample is introduced by the subject blowing into the inlet, or it may be introduced from a detachable container that has been previously filled with the breath sample. If necessary, a desiccating substance or semipermeable membrane may be included in the inlet path to remove water vapor from the sample; however, if an inlet tube of sufficient length is used, most water vapor will be removed by condensation along the length of the tube.

An exhaust outlet 56 exiting the second sample cell allows the sample to be removed, either by pumping, or, providing samples are sufficiently greater in volume than the sample cells, by introducing the next sample.

The first reference cell is connected to the second via a conduit 58, and to an inlet 60 through which purified air, or other purge gas, from which any ambient analyte molecule has been removed, can be introduced. For example, when the analyte molecule is $CO_2$, air may be circulated through a trap 62 containing NaOH or another metal hydroxide, typically an alkali or alkaline earth metal hydroxide, and optionally containing a desiccant.

Additional flow paths are set up within the enclosure 36 such that the purge gas may also be circulated within the enclosure, e.g. via outlet 63 and valve 64, including the air surrounding the source(s) and detector. Ambient levels of the analyte molecule which may be present in the air are thus prevented from affecting the intensity of radiation from the source by extraneous absorption. Valve 65 allows the sample cells to be purged between samples. The purge gas is circulated by means of a pump 66 and may be removed through exhaust outlet 68.

As an alternative to purging with purified air or other purge gas, the enclosure and/or the reference cells may be made fully airtight and evacuated. Evacuation of the enclosure, rather than flushing with a purge gas, has the advantage of ready adaptability to different analyte molecules, and eliminates the need for maintenance of a trap such as trap 62. The sample cells may also be evacuated between samples.

Vacuum activated shutters, as described above, may be used with this design if they are isolated from the evacuated portion of the enclosure, or the shutters may be operated by electromagnetic solenoids.

III. Method of Measuring Isotopic Ratios

A. General Method

In determining isotopic ratios according to the present invention, the concentration of each isotopic species is measured independently by measuring the absorbed intensity of radiation characteristic of the species passing through a sample cell and comparing it to the unattenuated intensity of the same radiation passing through a reference cell. The method thus includes transmitting IR radiation through four optical paths, specifically first and second sample paths, and first and second reference paths, as described above in Section IIB. The four optical paths may be provided by the use of bandpass filters, as described in Section IIB(1), or by the use of isotope-specific spectrally resolved sources, as described in Section IIB(2).

The concentration of each isotope is determined by measuring the intensity of radiation reaching the detector after being transmitted through the respective sample cell (intensity=I) relative to the intensity of similar radiation transmitted through the respective reference cell (intensity= $I_0$) The concentration at each absorption line is given by Beer's Law, $I/I_0 = e^{-\alpha CL}$, where $\alpha$ is the absorption coefficient for the species, C is the concentration, and L is the sample path length. In practice, when measuring a range of wavelengths, the net absorption does not follow Beer's Law exactly. Concentration is thus determined from the intensity ratios, $I/I_0$, based on previously determined calibration constants.

Each of the four optical paths of the invention, as described above, is traversed by source radiation in repeated rapid succession, preferably by means of vacuum activated shutters, to allow repeated measuring and averaging of the respective signals, with minimal opportunity for drift between measurements. Specifically, a concentration measurement is made for each isotope from the $I/I_0$ ratio for that isotope, and the ratio of concentrations (isotopic ratio) is determined after each successive pair of measurements. Finally, the many ratios so determined are averaged to give a single value of the isotopic ratio for the sample.

As noted above, sample path lengths may be adjusted so that the values of $I/I_0$ are not of greatly differing magnitudes for the different isotopes. Conversion of the intensity measurements at the detector to concentrations is easily accomplished by standard methods of computer analysis or via a dedicated microprocessor.

B. Crosstalk Corrections

If overlap exists between absorbance regions of the separate isotopes, adjustments for this crosstalk are generally required. Such adjustment will be described here for the measurement of the $^{13}CO_2/^{12}CO_2$ ratio, but a similar approach can be applied to correcting for crosstalk between isotopes of other molecules.

Figure 4:
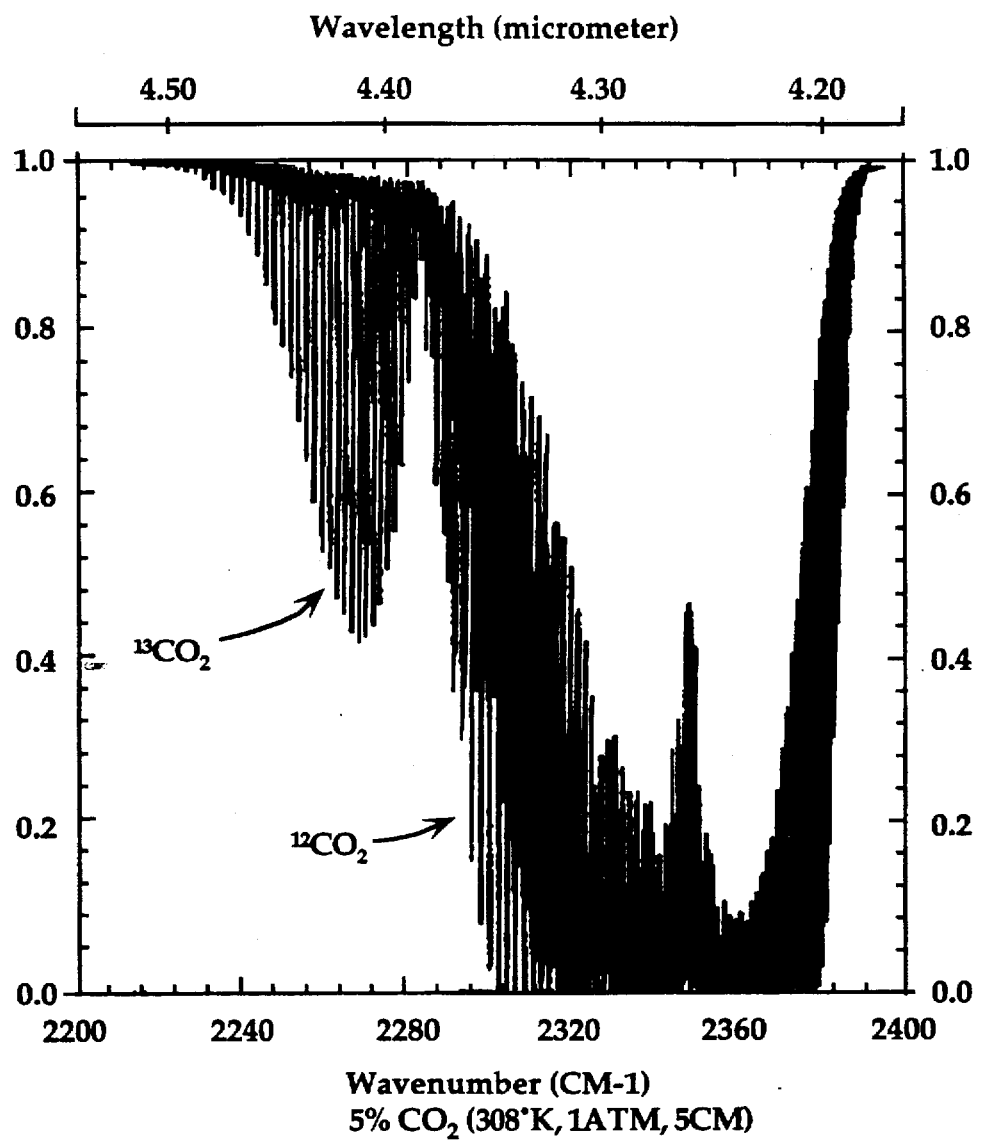
FIG. 4 shows the 4.2μ–4.5μ region of the $CO_2$ absorption spectrum, showing overlap between absorption of the isotopic species.

As shown in FIG. 4, the 4.2µ band of the abundant isotope, $^{12}CO_2$, overlaps that of the less abundant isotope, $^{13}CO_2$. As described above, narrow bandwidth filters may be used to select portions of the bands with minimal overlap for measurement of absorption. Preferably, the first beam, for measurement of $^{12}CO_2$, has a wavelength range between approximately 4.16µ and 4.39µ, and the second beam, for measurement of $^{13}CO_2$, has a wavelength range between approximately 4.30µ and 4.48µ. More preferably, the first beam has a wavelength range between approximately 4.16µ and 4.24µ, and the second beam has a wavelength range between approximately 4.38µ and 4.44µ.

At the typical relative abundances of $^{12}CO_2$ and $^{13}CO_2$, these wavelength ranges include a region of overlap at wavelengths greater than 4.38µ, as can be seen from FIG. 4.

Figure 5A:
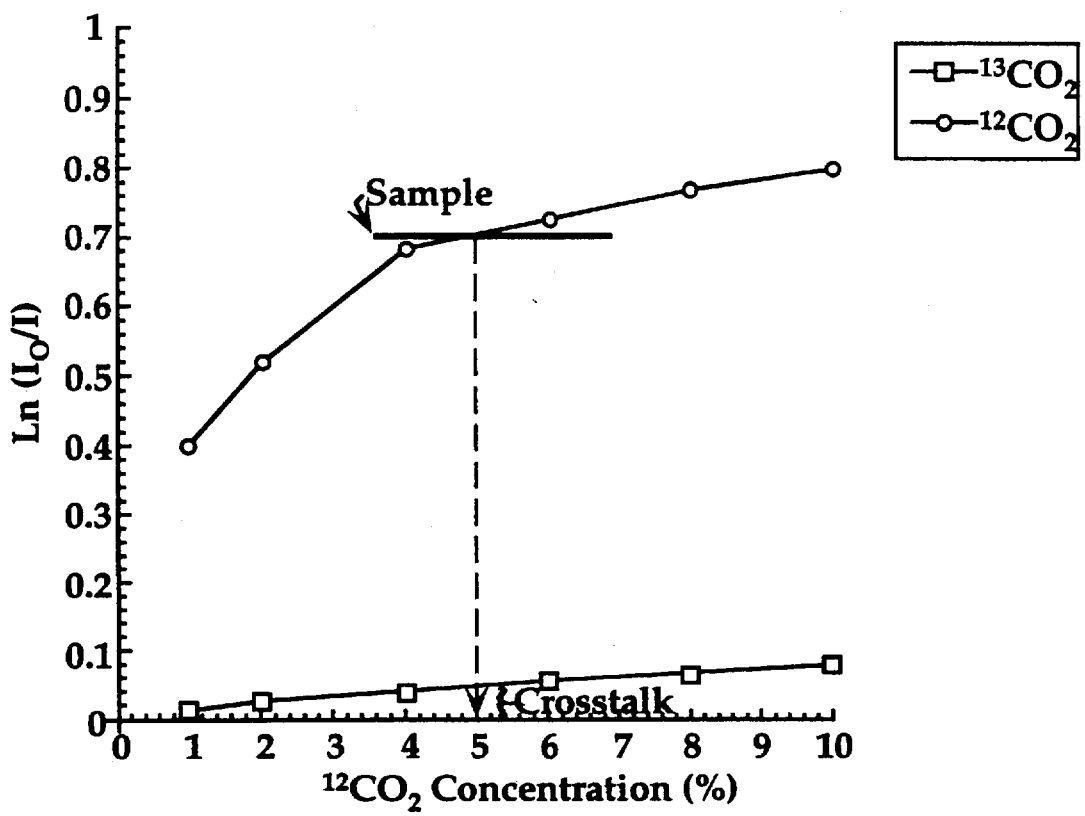
FIGS. 5A and 5B illustrate corrections for crosstalk in measurement of the $^{13}CO_2/^{12}CO_2$ ratio.
Figure 5B:
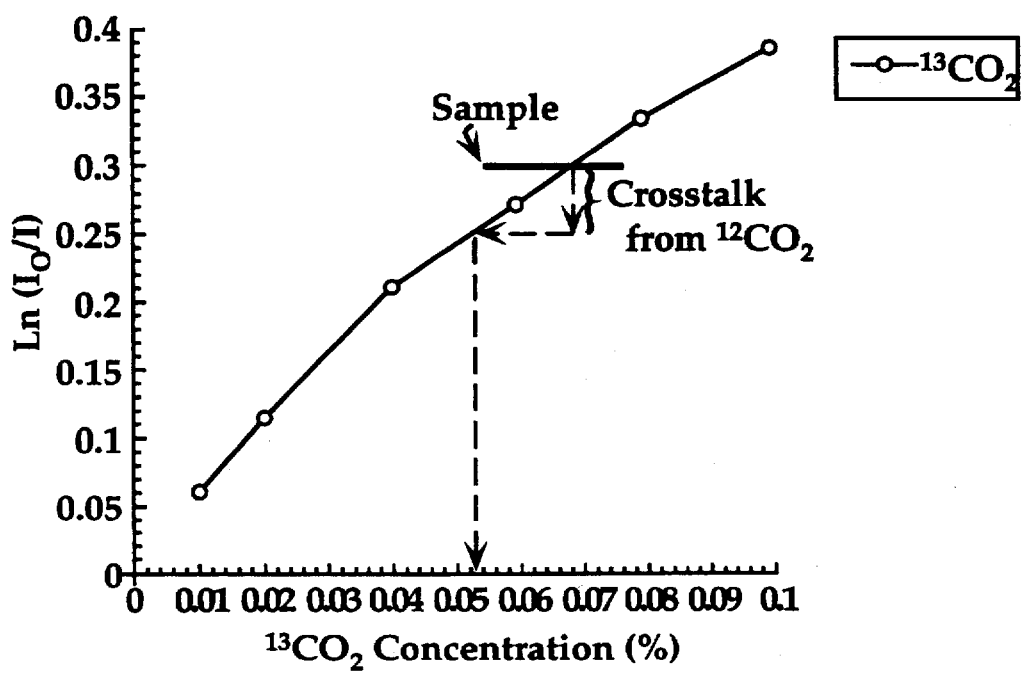

The contribution of $^{12}CO_2$ to absorbance in the $^{13}CO_2$ sample path is thus subtracted from the overall absorbance to obtain the absorbance due to $^{13}CO_2$ only. This correction can be calculated from the absorbance of the same sample in the $^{12}CO_2$ sample path, based on previously established calibration curves, as is illustrated in FIGS. 5A and 5B. Because the actual calibration curves will depend on factors such as the ratio of sample path lengths and the sample temperature for each device, the curves shown in FIG. 5 are for illustrative purposes only.

FIG. 5A shows typical calibration curves for absorption in the $^{13}CO_2$ optical path (lower curve) and in the $^{12}CO_2$ optical path (upper curve) for various levels of $^{12}CO_2$. A sample giving an absorbance ($\ln(I_0/I)$) value of 0.7 corresponds to approximately 5.0% $^{12}CO_2$, which will produce an absorbance of approximately 0.045 in the $^{13}CO_2$ optical path, as derived from the $^{13}CO_2$ curve. FIG. 5B shows the application of this correction to the $^{13}CO_2$ measurement, where the crosstalk correction of approximately 0.045 is subtracted from the absorbance measurement in the $^{13}CO_2$ optical path, to derive a corrected value of percent $^{13}CO_2$. These corrections can of course be carried out automatically by means of standard computer analysis.

If bandpass filters are not used, i.e. in the case of separate sources of isotope-specific radiation, where such filters are optional, the wavelength range of the radiation will cover the entire absorption band of the selected isotopic species, rather than a narrow region. However, in general, the individual lines of the absorption bands do not coincide between isotopic species, so only the isotope in the sample corresponding to the radiation source will absorb the radiation to any appreciable extent. In cases where crosstalk still occurs, however, corrections similar to those described above may then be made to eliminate the contribution from the interfering isotope, which will generally be the more abundant isotope.

C. Medical Applications

As noted above, measurement of isotopic ratios, in accordance with the present invention, can be applied to a number of biomedical applications, particularly in the area of diagnostics. In a typical procedure, an isotopically labeled substance is administered to a subject, and the level of label in the expired breath of the subject is measured to determine, for example, the extent of metabolism of the labeled substance.

The $^{13}CO_2/^{12}CO_2$ ratio is frequently measured in such analyses. In addition to the urea breath test for H. pylori infection, noted above, such diagnostic tests have been described for: pancreatic insufficiency, by administration of, for example, a labeled triglyceride (Watkins, 1977, Kato); gastric emptying rates, by administration of labeled octanoates (Ghoos); fat malabsorption (Watkins, 1977); small intestine bacterial overgrowth, using labeled xylose (Solomons, King); glucose utilization (Lacroix); starch utilization (Shulman); and cirrhosis (Shreeve). Several tests have been described for liver disfunction in general, which generally measure the activity of various P450 enzymes. These include the aminopyrine test (Mion), the caffeine test (Lambert), and the erythromycin test (Watkins, 1990).

Although expired $CO_2$ is a convenient vehicle for diagnostic testing, tests employing measurement of isotopic ratios of other species have also been described. These include, for example, the use of $^{15}N$ in measuring protein turnover (Waterlow) and the use of doubly labeled $H_2O$ in measuring energy expenditure (Schoeller, 1982).

While the invention has been described with reference to specific methods and embodiments, it will be appreciated that various modifications may be made without departing from the invention.

It is claimed:

1. An apparatus for measuring the ratio of first and second isotopic species of an analyte molecule in a gaseous sample by non-dispersive IR spectroscopy, comprising at least one source of IR radiation;

first and second, interconnected sample cells containing the gaseous sample;

at least one reference cell free of the analyte molecule;

at least one IR detector;

means for providing four optical paths of said radiation impinging on said at least one detector, said optical paths comprising a first sample path traversing the first sample cell and having a first wavelength range characteristic of the first isotopic species, a first reference path traversing a reference cell and having a first wavelength range characteristic of the first isotopic species, a second sample path traversing the second sample cell and having a second wavelength range characteristic of the second isotopic species, and a second reference path traversing a reference cell and having a second wavelength range characteristic of the second isotopic species;

means for directing radiation through each of said cells;

shutter means effective to permit radiation to traverse each of said paths in rapid succession; and means for directing radiation from each of said paths onto said at least one detector;

whereby the ratio of said isotopic species is determined by comparison of the intensity of radiation impinging on said at least one detector from said paths.

2. The apparatus of claim 1, comprising a single source of IR radiation.

3. The apparatus of claim 1, comprising a single detector.

4. The apparatus of claim 1, wherein said directing means comprise IR transparent lenses.

5. The apparatus of claim 1, wherein said shutter means are vacuum activated shutters.

6. The apparatus of claim 1, wherein said providing means comprises positioned in said first sample path and said first reference path, at least one bandpass filter effective to restrict the IR radiation transmitted to said at least one detector from said first paths to a narrow wavelength range characteristic of said first isotopic species; and positioned in said second sample path and said second reference path, at least one bandwidth filter effective to restrict the IR radiation transmitted to said at least one detector from said second paths to a narrow wavelength range characteristic of said second isotopic species.

7. The apparatus of claim 1, comprising two sources of IR radiation, wherein said sources comprise a first spectrally resolved source, comprising the first isotopic species of said analyte molecule and means for vibrationally exciting said first isotopic species, thereby causing it to radiate at at least one wavelength characteristic of said first species; and a second spectrally resolved source, comprising the second isotopic species of said analyte molecule and means for vibrationally exciting said second isotopic species, thereby causing it to radiate at at least one wavelength characteristic of said second species.

8. The apparatus of claim 7, wherein said isotopic species are vibrationally excited via an electronic discharge.

9. The apparatus of claim 8, wherein the electronic discharge is electronically modulated.

10. The apparatus of claim 7, wherein said isotopic species are vibrationally excited via an external heat source.

11. The apparatus of claim 1, comprising a first pair of cells, consisting of a first sample cell containing the gaseous sample, and a first reference cell free of the analyte molecule, and a second pair of cells, consisting of a second sample cell containing the gaseous sample, and a second reference cell free of the analyte molecule.

12. The apparatus of claim 11, further comprising a flow path entering one of said sample cells, connecting the sample cells, and exiting the other of said sample cells, such that the gaseous sample is maintained at a composition and pressure which is equal in the first sample cell and the second sample cell.

13. The apparatus of claim 11, wherein the first isotopic species of the analyte molecule has a greater natural abundance than the second isotopic species, the first sample cell has a length L1, the second sample cell has a length L2, and L1<L2.

14. The apparatus of claim 1, wherein said cells are contained within an enclosure effective to control cell temperature to within approximately 0.1° C.

15. The apparatus of claim 14, further comprising means for removal of ambient analyte molecule from said enclosure.

16. The apparatus of claim 1, wherein said analyte molecule is $CO_2$, said first isotopic species is $^{12}CO_2$, and said second isotopic species is $^{13}CO_2$.

17. A method for measuring the ratio of first and second isotopic species of an analyte molecule in a gaseous sample by non-dispersive IR spectroscopy, comprising transmitting IR radiation through four optical paths which impinge on at least one IR detector, said optical paths comprising a first sample path traversing a first sample cell containing the gaseous sample and having a first wavelength range characteristic of the first isotopic species, a first reference path traversing a reference cell free of the analyte molecule and having a first wavelength range characteristic of the first isotopic species, a second sample path traversing a second sample cell, which is interconnected with said first sample cell, and having a second wavelength range characteristic of the second isotopic species, and a second reference path traversing a reference cell free of the analyte molecule and having a second wavelength range characteristic of the second isotopic species;

determining the concentration of the first isotopic species from the intensity of radiation received at the detector from the first sample path relative to the intensity of radiation received at the detector from the first reference path;

determining the concentration of the second isotopic species from the intensity of radiation received at the detector from the second sample path relative to the intensity of radiation received at the detector from the second reference path; and determining from said concentrations the ratio of said isotopic species in the gaseous sample.

18. The method of claim 17, wherein each of said optical paths is traversed in repeated rapid succession.

19. The method of claim 16, wherein said optical paths are provided by positioning in said first sample path and said first reference path, at least one bandpass filter effective to restrict the IR radiation transmitted to said at least one detector from said first paths to a narrow wavelength range characteristic of said first isotopic species; and positioning in said second sample path and said second reference path, at least one bandpass filter effective to restrict the IR radiation transmitted to said at least one detector from said second paths to a narrow wavelength range characteristic of said second isotopic species.

20. The method of claim 16, wherein said optical paths are provided by vibrationally exciting said first isotopic species, thereby causing it to emit radiation at at least one wavelength characteristic of said first species, and directing said radiation through a sample cell and a reference cell, thereby providing the first sample path and the first reference path; and vibrationally exciting said second isotopic species, thereby causing it to radiate at at least one wavelength characteristic of said species, and directing said radiation through a sample cell and a reference cell, thereby providing the second sample path and the second reference path.

21. The method of claim 17, further comprising the step of correcting for crosstalk resulting from absorption of one isotopic species at a wavelength range characteristic of the other isotopic species.

22. The method of claim 17, wherein said analyte molecule is $CO_2$, said first isotopic species is $^{12}CO_2$, and said second isotopic species is $^{13}CO_2$.

23. The method of claim 17, for use in breath analysis, wherein the gaseous sample comprises the expired breath of a subject to whom an isotopically labelled substance has been previously administered.

* * * * *